United States Patent
Tkaczyk et al.

(10) Patent No.: US 7,433,443 B1
(45) Date of Patent: Oct. 7, 2008

(54) SYSTEM AND METHOD OF CT IMAGING WITH SECOND TUBE/DETECTOR PATCHING

(75) Inventors: John Eric Tkaczyk, Delanson, NY (US); Samit Kumar Basu, Niskayuna, NY (US); Xiaoye Wu, Rexford, NY (US); Yanfeng Du, Rexford, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/846,664

(22) Filed: Aug. 29, 2007

(51) Int. Cl.
*H05G 1/26* (2006.01)

(52) U.S. Cl. .............................. 378/19; 378/9

(58) Field of Classification Search ............ 378/4, 378/9, 19; 250/390.09, 370.1
See application file for complete search history.

(56) References Cited

U.S. PATENT DOCUMENTS

2005/0031075 A1* 2/2005 Hopkins et al. .............. 378/57
2005/0067578 A1* 3/2005 Ueno et al. ............. 250/370.09
2008/0061395 A1* 3/2008 Tkaczyk et al. ............. 257/443

* cited by examiner

*Primary Examiner*—Hoon Song
(74) *Attorney, Agent, or Firm*—Jason K. Klindtworth (57) ABSTRACT

A CT imaging system includes a rotatable gantry having an opening to receive an object to be scanned, a first x-ray emission source attached to the rotatable gantry and configured to emit x-rays toward the object, and a second x-ray emission source attached to the rotatable gantry and configured to emit x-rays toward the object. A first detector is configured to receive x-rays that emit from the first x-ray emission source, and a second detector configured to receive x-rays that emit from the second x-ray emission source. A first portion of the first detector is configured to operate in an integration mode and a first portion of the second detector is configured to operate in at least a photon-counting mode.

25 Claims, 5 Drawing Sheets

SYSTEM AND METHOD OF CT IMAGING WITH SECOND TUBE/DETECTOR PATCHING

BACKGROUND OF THE INVENTION

The present invention relates generally to diagnostic imaging and, more particularly, to a system and method of correcting saturated data occurring in photon-counting and configurable mode detectors.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

In most computed tomography (CT) imaging systems, the x-ray source and the detector array are rotated about a gantry encompassing an imaging volume around the subject. X-ray sources typically include x-ray tubes, which emit the x-rays as a fan or cone beam from the anode focal point. X-ray detector assemblies typically include a collimator for reducing scattered x-ray photons from reaching the detector, a scintillator adjacent to the collimator for converting x-rays to light energy, and a photodiode adjacent to the scintillator for receiving the light energy and producing electrical signals therefrom. Typically, each scintillator of a scintillator array converts x-rays to light energy. Each photodiode detects the light energy and generates a corresponding electrical signal. The outputs of the photodiodes are then transmitted to the data acquisition system and then to the processing system for image reconstruction.

Conventional CT imaging systems utilize detectors that convert x-ray photon energy into current signals that are integrated over a time period, then measured and ultimately digitized. A drawback of such detectors is their inability to provide independent data or feedback as to the energy and incident flux rate of photons detected. That is, conventional CT detectors have a scintillator component and photodiode component wherein the scintillator component illuminates upon reception of x-ray photons and the photodiode detects illumination of the scintillator component and provides an integrated electrical current signal as a function of the intensity and energy of incident x-ray photons. While it is generally recognized that CT imaging would not be a viable diagnostic imaging tool without the advancements achieved with conventional CT detector design, a drawback of these integrating detectors is their inability to provide energy discriminatory data or otherwise count the number and/or measure the energy of photons actually received by a given detector element or pixel. Accordingly, recent detector developments have included the design of an energy discriminating detector that can provide photon counting and/or energy discriminating feedback. In this regard, the detector can be caused to operate in an x-ray counting mode, an energy measurement mode of each x-ray event, or both.

These energy discriminating detectors are capable of not only x-ray counting, but also providing a measurement of the energy level of each x-ray detected. While a number of materials may be used in the construction of an energy discriminating detector, including scintillators and photodiodes, direct conversion detectors having an x-ray photoconductor, such as amorphous selenium or cadmium zinc telluride, that directly convert x-ray photons into an electric charge have been shown to be among the preferred materials. A drawback of photon counting detectors is that these types of detectors have limited count rates and have difficulty covering the broad dynamic ranges encompassing very high x-ray photon flux rates typically encountered with conventional CT systems. Generally, a CT detector dynamic range of 1,000,000 to one is required to adequately handle the possible variations in photon flux rates encountered in CT imaging. In the fast scanners now available, it is not uncommon to encounter x-ray fluxes of over $10^8$ photons/mm2/sec when no object is in the scan field, with the same detection system needing to count only tens of photons that manage to traverse the center of large objects.

The very high x-ray photon fluxes ultimately lead to detector saturation. That is, these detectors typically saturate at relatively low x-ray flux levels. This saturation can occur at detector locations wherein small subject thickness is interposed between the detector and the radiation source or x-ray tube. It has been shown that these saturated regions correspond to paths of low subject thickness near or outside the width of the subject projected onto the detector array. In many instances, the subject is more or less cylindrical in the effect on attenuation of the x-ray flux and subsequent incident intensity to the detector array. In this case, the saturated regions represent two disjointed regions at extremes of the detector array. In other less typical, but not rare instances, saturation occurs at other locations and in more than two disjointed regions of the detector. In the case of a cylindrical subject, the saturation at the edges of the array can be reduced by the imposition of a bowtie filter between the subject and the x-ray source. Typically, the filter is constructed to match the shape of the subject in such a way as to equalize total attenuation, filter and subject, across the detector array. The flux incident to the detector is then relatively uniform across the array and does not result in saturation. What can be problematic, however, is that the bowtie filter may not be optimum given that a subject population is significantly less than uniform and not exactly cylindrical in shape nor centrally located in the x-ray beam. In such cases, it is possible for one or more disjointed regions of saturation to occur or conversely to over-filter the x-ray flux and unnecessarily create regions of very low flux. Low x-ray flux in the projection results in a reduction in information content which will ultimately contribute to unwanted noise in the reconstructed image of the subject.

A number of techniques have been proposed to address saturation of any part of the detector. These techniques include maintenance of low x-ray flux across the width of a detector array, for example, by modulating tube current or x-ray voltage during scanning. However, this solution leads to increased scan time. That is, there is a penalty in that the acquisition time for the image is increased in proportion to the nominal flux needed to acquire a certain number of x-rays that meet image quality requirements.

Furthermore, configurable mode detectors have been developed that are capable of operating in either integrating or photon-counting modes, where the data processing method changes from photon-counting mode to integrating mode in high-flux portions of the detector. However, for configurable mode detectors the full dynamic range may not be available and saturation may yet occur.

Systems with multiple source/detector sub-systems have been built in order to improve temporal resolution. However, these systems do not include photon-counting capability, nor do such systems have the capability to re-bin or simultaneously correct the saturated data in one detector sub-system with data from an unsaturated detector sub-system.

Therefore, it would be desirable to have a system and method capable of correcting saturated data occurring in photon-counting and configurable mode detectors using data from non-saturated detectors in a multiple source/detector CT system.

BRIEF DESCRIPTION OF THE INVENTION

The present invention is a directed method and apparatus for correcting saturated data occurring in photon-counting and configurable mode detectors using data from non-saturated detectors in a multiple source/detector CT system.

A spectral CT system with second tube/detector data patching is disclosed. The CT detector includes a semi-conductor layer having a plurality of pixelated anodes attached thereto. The CT detector supports not only x-ray photon counting, but energy measurement or tagging and energy integration as well. As a result, the present invention supports the acquisition of both anatomical detail as well as tissue characterization information. In this regard, the energy discriminatory information or data may be used to reduce the effects of beam hardening and the like. Furthermore, these detectors support the acquisition of tissue discriminatory data and therefore provide diagnostic information that is indicative of disease or other pathologies. This detector can also be used to detect, measure, and characterize materials that may be injected into the subject such as contrast agents and other specialized materials by the use of optimal energy weighting to boost the contrast of iodine and calcium (and other high atomic or materials). Contrast agents can, for example, include iodine that is injected into the blood stream for better visualization.

According to an aspect of the present invention a CT imaging system includes a rotatable gantry having an opening to receive an object to be scanned, a first x-ray emission source attached to the rotatable gantry and configured to emit x-rays toward the object, and a second x-ray emission source attached to the rotatable gantry and configured to emit x-rays toward the object. A first detector is configured to receive x-rays that emit from the first x-ray emission source, and a second detector configured to receive x-rays that emit from the second x-ray emission source. A first portion of the first detector is configured to operate in an integration mode and a first portion of the second detector is configured to operate in at least a photon-counting mode.

According to another aspect of the present invention, a method of x-ray imaging includes receiving x-rays in a first segment of a first detector array, the x-rays emitting from a first x-ray source that pass through at least a portion of an imaging region and receiving x-rays in a first segment of a second detector array, the x-rays emitting from a second x-ray source that pass through at least a portion of the imaging region. The method further includes operating the first segment of the first detector array in an integrating mode to generate a first set of data from received x-rays, operating the first segment of the second detector array in a photon-counting mode to generate a second set of data from received x-rays, and generating an image using the first and second sets of data.

According to yet another aspect of the present invention a CT imaging system includes a gantry configured to rotate about a subject and a pair of sources attached to the gantry configured to emit high frequency electromagnetic radiation toward the subject. A first array of detector modules is configured to receive high frequency electromagnetic radiation that emits from a first source of the pair of sources and passes through the subject, and a second detector module configured to receive high frequency electromagnetic radiation that emits from a second source of the pair of sources and passes through the subject. The first detector module is configured to operate in at least an integration mode and the second detector module is configured to operate in at least a photon-counting mode.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

Diagnostics devices comprise x-ray systems, magnetic resonance (MR) systems, ultrasound systems, computed tomography (CT) systems, positron emission tomography (PET) systems, ultrasound, nuclear medicine, and other types of imaging systems. Applications of x-ray sources comprise imaging, medical, security, and industrial inspection applications. However, it will be appreciated by those skilled in the art that an implementation is applicable for use with single-slice or other multi-slice configurations. Moreover, an implementation is employable for the detection and conversion of x-rays. However, one skilled in the art will further appreciate that an implementation is employable for the detection and conversion of other high frequency electromagnetic energy. An implementation is employable with a "third generation" CT scanner and/or other CT systems.

The operating environment of the present invention is described with respect to a sixty-four-slice computed tomography (CT) system. However, it will be appreciated by those skilled in the art that the present invention is equally applicable for use with other multi-slice configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems.

Figure 1:
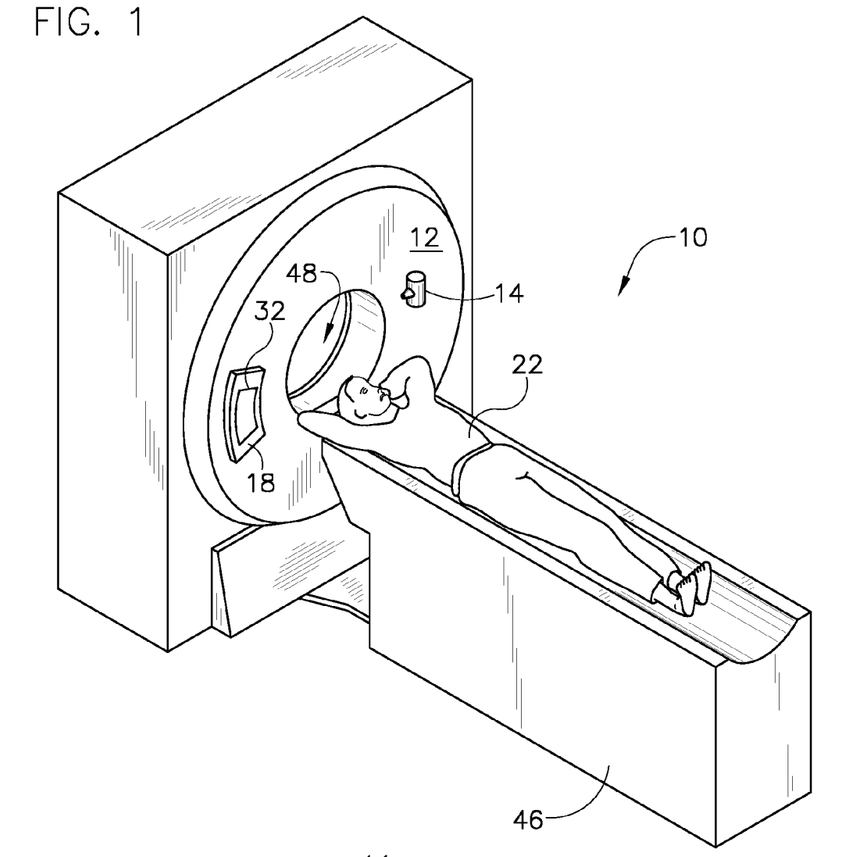
FIG. 1 is a pictorial view of a CT imaging system.
Figure 2:
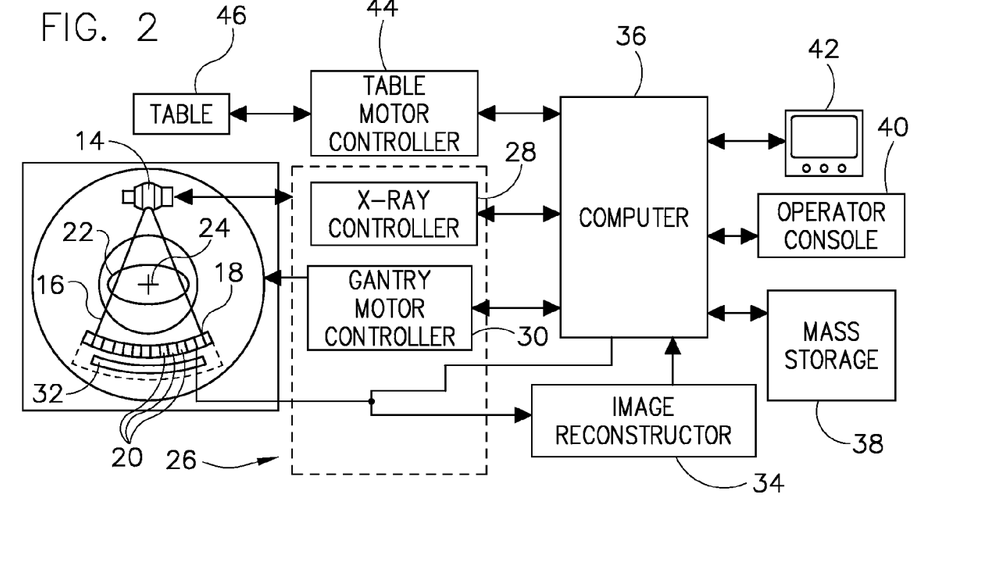
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays 16 toward a detector assembly or collimator 18 on the opposite side of the gantry 12. Referring now to FIG. 2, detector assembly 18 is formed by a plurality of detectors 20 and data acquisition systems (DAS) 32. The plurality of detectors 20 sense the projected x-rays that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
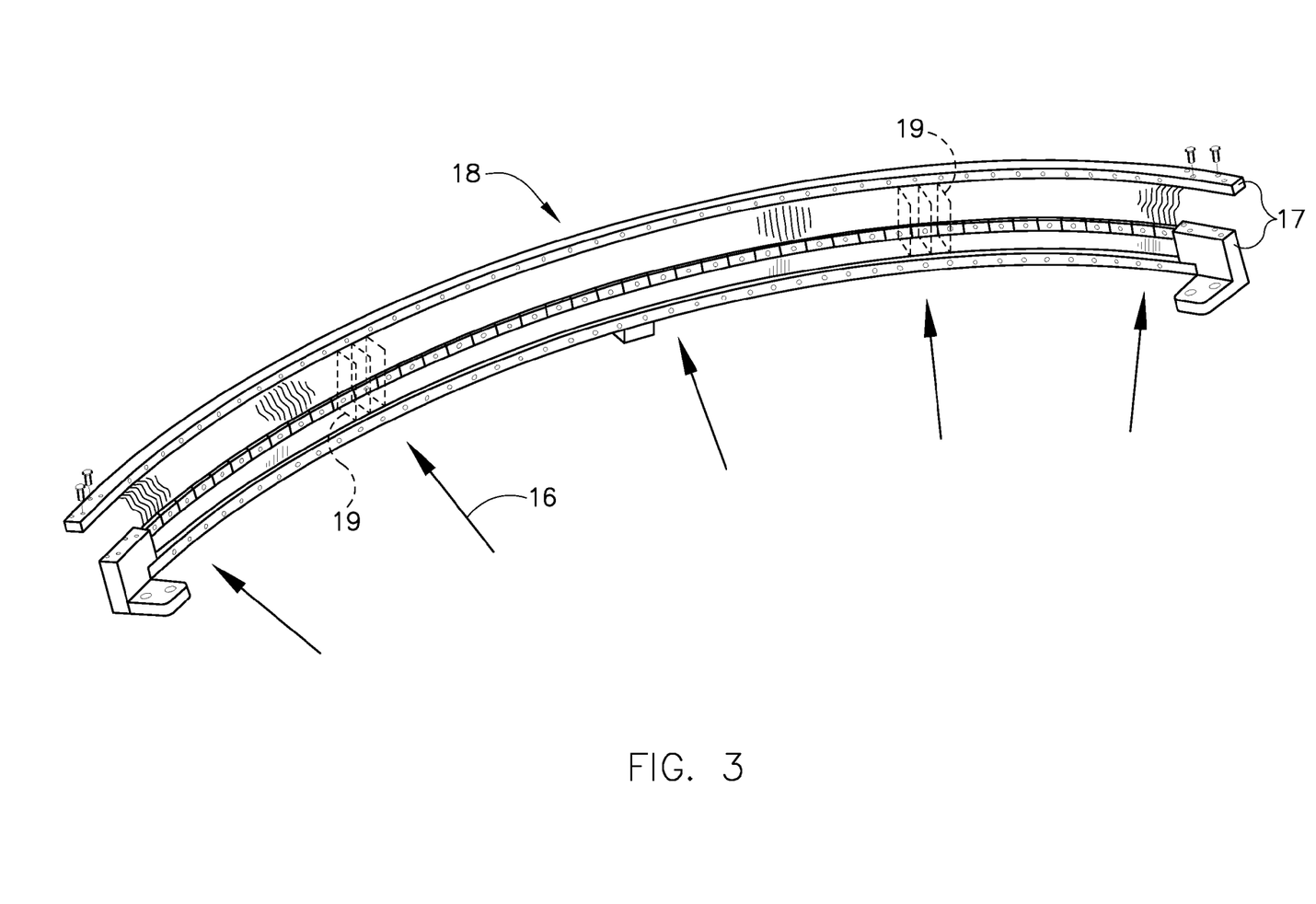
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 columns (16×57 detectors) which allows 64 simultaneous slices of data to be collected with each rotation of gantry 12.

Figures 4, 5:
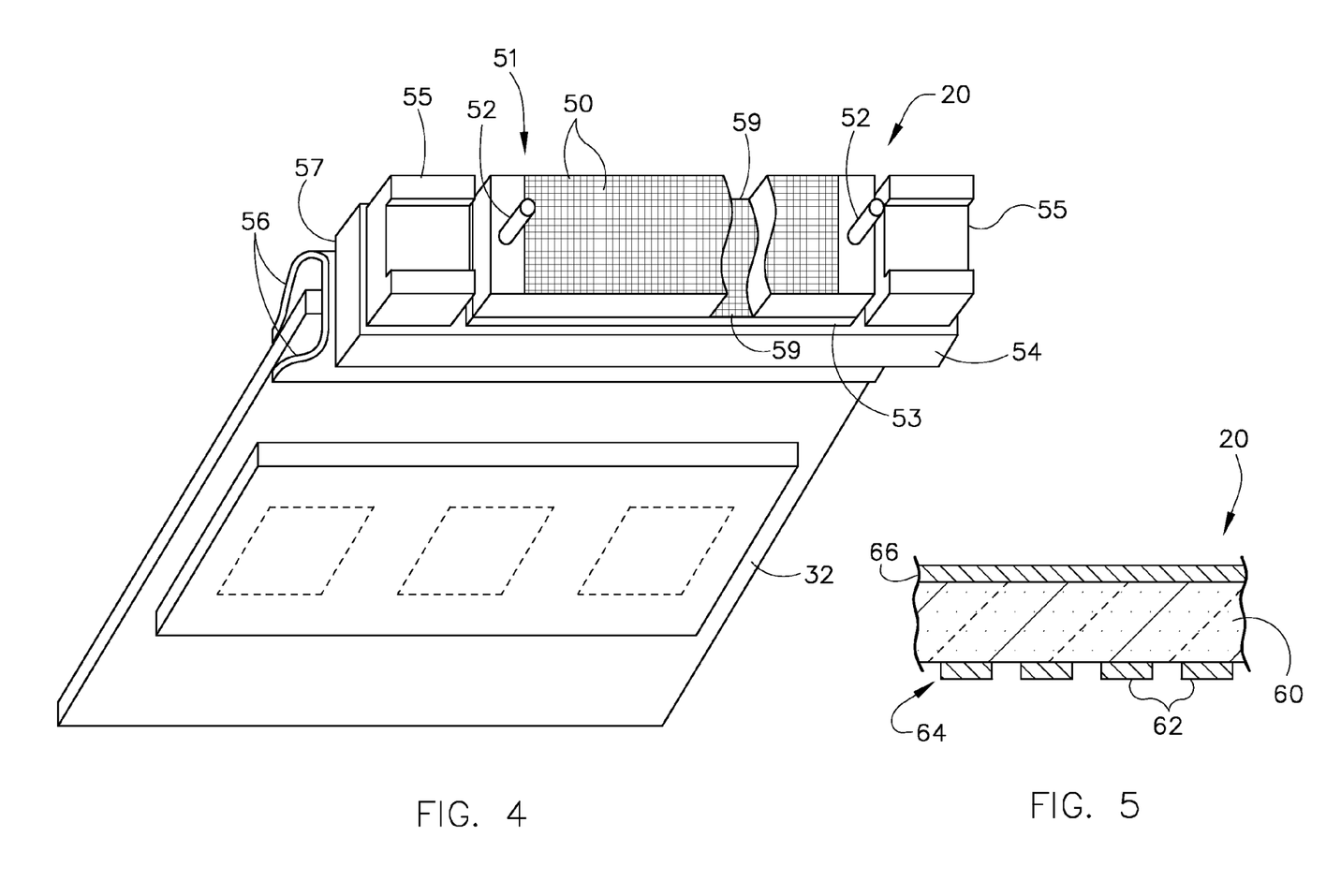
FIG. 4 is a perspective view of one embodiment of a detector.
FIG. 5 is a side view of one embodiment of a direct conversion detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is integrated and converted to a digital signal.

Each detector 20 may in the alternative be designed to directly convert radiographic energy to electrical signals containing energy discriminatory or photon count data. Such detectors are typically referred to as "direct conversion" devices. Direct conversion devices may likewise be configured to operate in integration mode as well. Such devices may be referred to as configurable. In a preferred embodiment, each detector 20 includes a semiconductor layer fabricated from CZT. Each detector 20 also includes a plurality of metallized anodes attached to the semiconductor layer. As will be described, such detectors 20 may include an electrical circuit having multiple comparators thereon which may reduce statistical error due to pileup of multiple energy events.

Referring now to FIG. 5, a portion of a CZT or direct conversion detector in accordance with one embodiment of the present invention is shown. Detector 20 is defined by a semiconductor layer 60 having a number of electronically pixelated structures or pixels to define a number of detector elements, anodes, or contacts 62. This electronic pixelation is accomplished by applying a 2D array 64 of electrical contacts 62 onto a layer 60 of direct conversion material.

Detector 20 includes a contiguous high-voltage electrode 66 attached to semiconductor layer 60. The high-voltage electrode 66 is connected to a power supply (not shown) and it is designed to power the semiconductor layer 60 during the x-ray detection process. One skilled in the art will appreciate that the high-voltage layer 66 should be relatively thin so as to reduce the x-ray absorption characteristics and, in a preferred embodiment, is a few hundred angstroms in thickness. In a preferred embodiment, the high-voltage electrode 66 may be affixed to the semiconductor layer 60 through a metallization process. X-ray photons that impinge upon the semiconductor layer 60 will generate an electrical charge therein, which is collected in one or more of the electrical contacts 62, and which may be read out to the DAS 32 of FIG. 2. The amplitude of the charge collected is indicative of the energy of the photon that created the charge.

An integrating detector or a photon-counting detector operating in integration mode provide a CT number or Hounsfield value. An energy selective or energy discriminating system CT system, on the other hand, can provide additional information related to a material's atomic number and density. This information may be particularly useful for a number of medical clinical applications, where the CT number of different materials may be similar but the atomic number may be quite different. For example, calcified plaque and iodine-contrast enhanced blood may be located together in coronary arteries or other vessels. As will be appreciated by those skilled in the art, calcified plaque and iodine-contrast enhanced blood are known to have distinctly different atomic numbers, but at certain densities these two materials are indistinguishable by CT number alone.

Because of the different saturation levels and increased saturation threshold of integrating detectors as compared to photon-counting detectors, saturated regions of a photon-counting detector may occur at flux levels below which saturation occurs in an energy integrating detector. Additionally, even though a photon-counting detector may be configured to operate in integration mode, such operation has limited dynamic range and may not suffice to avoid saturation. As such, a combination of detector types may be employed in a two-source/two-detector arrangement in order to patch saturated regions of one detector with non-saturated data from a second detector, and to preserve the highest dose utilization.

Figure 6:
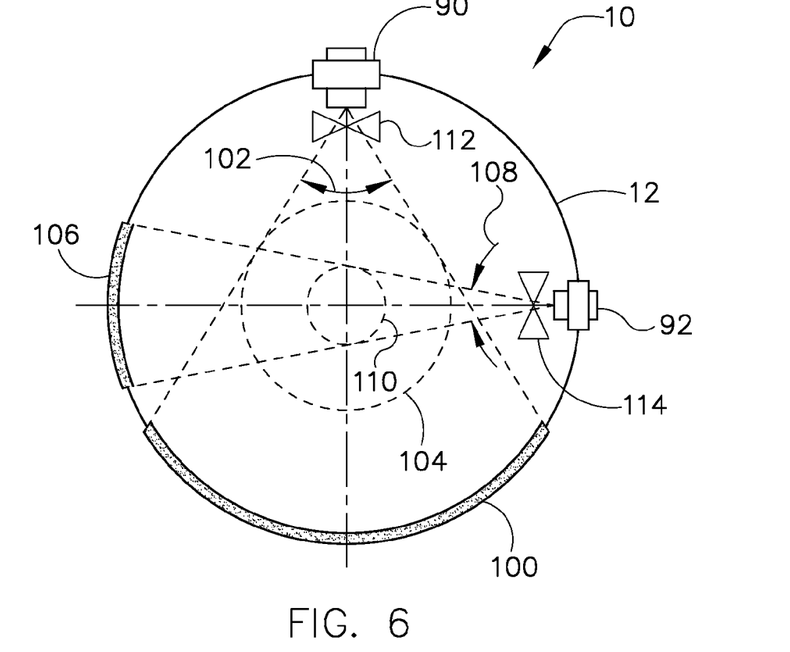
FIG. 6 illustrates a gantry having two sources and two detector arrays according to an embodiment of the present invention.

Referring now to FIG. 6, an axial view of a CT gantry 10 is illustrated according to an embodiment of the present invention. Gantry 12 includes a first x-ray source 90 and a second x-ray source 92. In this embodiment, a first detector 100 receives data over arc 102 in order to receive data passing through a first field-of-view (FOV) 104. A second detector 106 receives data over arc 108 in order to receive data passing through a second FOV 110. In this embodiment, the second FOV 110 is smaller than the first FOV 104. However, one skilled in the art will recognize that the two FOVs 104, 110 may be equal in size or that the second FOV 110 may be larger than the first FOV 104, depending on arcs of coverage 102, 108 achieved in detectors 100, 106. Variable bowtie filters 112, 114 may optionally be placed between one or both x-ray sources 90, 92 and their respective detectors 100, 106. One skilled in the art will recognize that detectors having saturation thresholds higher than, for instance, a photon-counting detector, such as an integrating detector, may not require a bowtie filter.

According to an embodiment of the present invention, detector 100 covering the FOV 104 is a scintillator-based integrating detector, and the second detector 106 covering the FOV 110 is a direct-conversion, photon-counting detector. Because the saturation thresholds of the two detectors are different and the saturation threshold in the direct-conversion detector tends to be lower, portions of the direct conversion detector 106 will tend to saturate at a given flux level, despite the presence of the bowtie filter 114. However, because of the increased dynamic range capability of the integrating detector 100, detector 100 will tend not to saturate at a comparable flux level, thus providing data that may be used to patch saturated regions of detector 106 that occurs within the FOV 110.

In other words, when the second detector 106 saturates, because the corresponding FOV 110 of the second detector 106 is smaller than the FOV 104 of the larger detector 100 and because the first detector 100 has a higher flux capability, data obtained therein may be used to correct data that is otherwise lost in the photon-counting detector 106. One skilled in the art would recognize that data taken from the one detector 100 and patched into the second detector 106 must be appropriately registered to account for the two gantry angles at which data is acquired.

Figure 7:
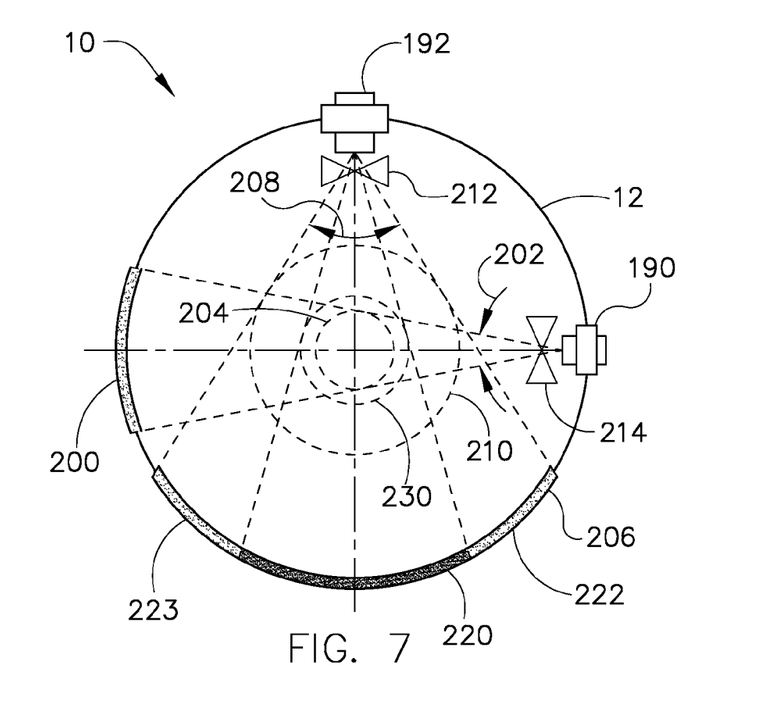
FIG. 7 illustrates a gantry having two sources and two detector arrays according to another embodiment of the present invention.

Referring now to FIG. 7, an axial view of a CT gantry 10 is illustrated according to another embodiment of the present invention. Gantry 12 includes a first x-ray source 190 and a second x-ray source 192. In this embodiment, a first detector 200 receives data over arc 202 in order to receive data passing through a first FOV 204. A second, segmented-arc detector 206 receives data over arc 208 in order to receive data passing through a second FOV 210. In this embodiment, the first FOV 204 is smaller than the second FOV 210. However, one skilled in the art will recognize that the two FOVs 204, 210 may be equal in size or that the second FOV 210 may be smaller than the first FOV 204, depending on arcs of coverage 202, 208 achieved in detectors 200, 206. Variable bowtie filters 212, 214 may optionally be placed between one or both x-ray sources 190, 192 and their respective detectors 200, 206. One skilled in the art will recognize that detectors having saturation thresholds higher than for instance a photon-counting detector, such as an integrating detector, may not require a bowtie filter.

In an embodiment, detector 200 may be a scintillating-based integrating detector or a photon-counting detector configurable to operate in either integrating or photon-counting mode. Segmented-arc detector 206, on the other hand, has a first segment 220 and second segments 222, 223. According to an embodiment of the present invention, first segment 220 is configured to operate in a different processing mode than second segments 222, 223. In this manner, first segment 220 may be a configurable energy discriminating detector segment configured to operate in photon-counting mode, and second segments 222, 223 may be scintillating-based integrating detectors or configurable energy discriminating detector segments configured to operate in integrating mode. As such, detector 206 may have a secondary FOV 230 defined by first segment 220 contained within the second FOV 210. Although the secondary FOV 230 is illustrated as having a smaller diameter than FOV 204 that corresponds to first detector 200, one skilled in the art will recognize that FOVs 204, 230 may likewise have comparable diameters or that secondary FOV 230 may have a diameter smaller than that of FOV 204.

Because the saturation threshold of detectors in segment 220 is different from the saturation threshold of detectors in segments 222, 223, portions of the first segment 220 will tend to saturate at a given flux level lower than that of detector 200 despite the presence of the bowtie filter 212. However, because of the increased dynamic range capability of the detector 200, detector 200 will tend not to saturate at a comparable flux level, thus providing data that may be used to patch saturated regions of detector segment 220 that occurs within FOV 230.

In other words, when data saturates in the first segment 220, data in detector 200 may be used to correct data that is otherwise lost in the photon-counting section 220. One skilled in the art would recognize that data taken from detector 200 and patched into the second detector segment 220 must be appropriately registered to account for the two gantry angles at which data is acquired.

In the embodiments described herein, correction of data may be accomplished by use of an iterative reconstruction technique. In this technique, correction of saturated data begins by making an initial guess or trial on the image of the object under study. The method forward projects the trial image using a system model in order to obtain the expected data. The difference between the expected data to the actual measured data generates an error that is used to adjust the trial images. The procedure is repeated to better match the expected data to the measured data up to a limit of accuracy or number of iterations.

In the embodiments described herein, data patching may be performed by accounting for the difference in gantry angle between the respective detectors and interpolating accordingly. For axial scanning, data is rebinned by accounting for the difference in gantry angle based on whether the acquired data is offset by an integer number of views. If the two detectors are offset by an integer number of views, then re-binning is performed by simply shifting the dataset by the integer number of offset views. If the two detectors are not offset by an integer number of views, then data from one detector on one set of gantry angles is linearly interpolated onto the gantry angle set of the second detector.

For helical scanning a more elaborate interpolation is needed. That is, when a source/detector subsystem is at a first angle A at a time T, then the second source/detector subsystem does not reach angle A until time T+delta. During this time interval delta, the patient is translated so that the views through the patient are not equivalent (as they are in an axial scan). The data, instead, is a function of a two-dimensional discrete set of angles and the patient position along Z. Thus, the interpolation must account for the view position of the detectors and the patient position along the Z-axis during a helical scan.

Figure 8:
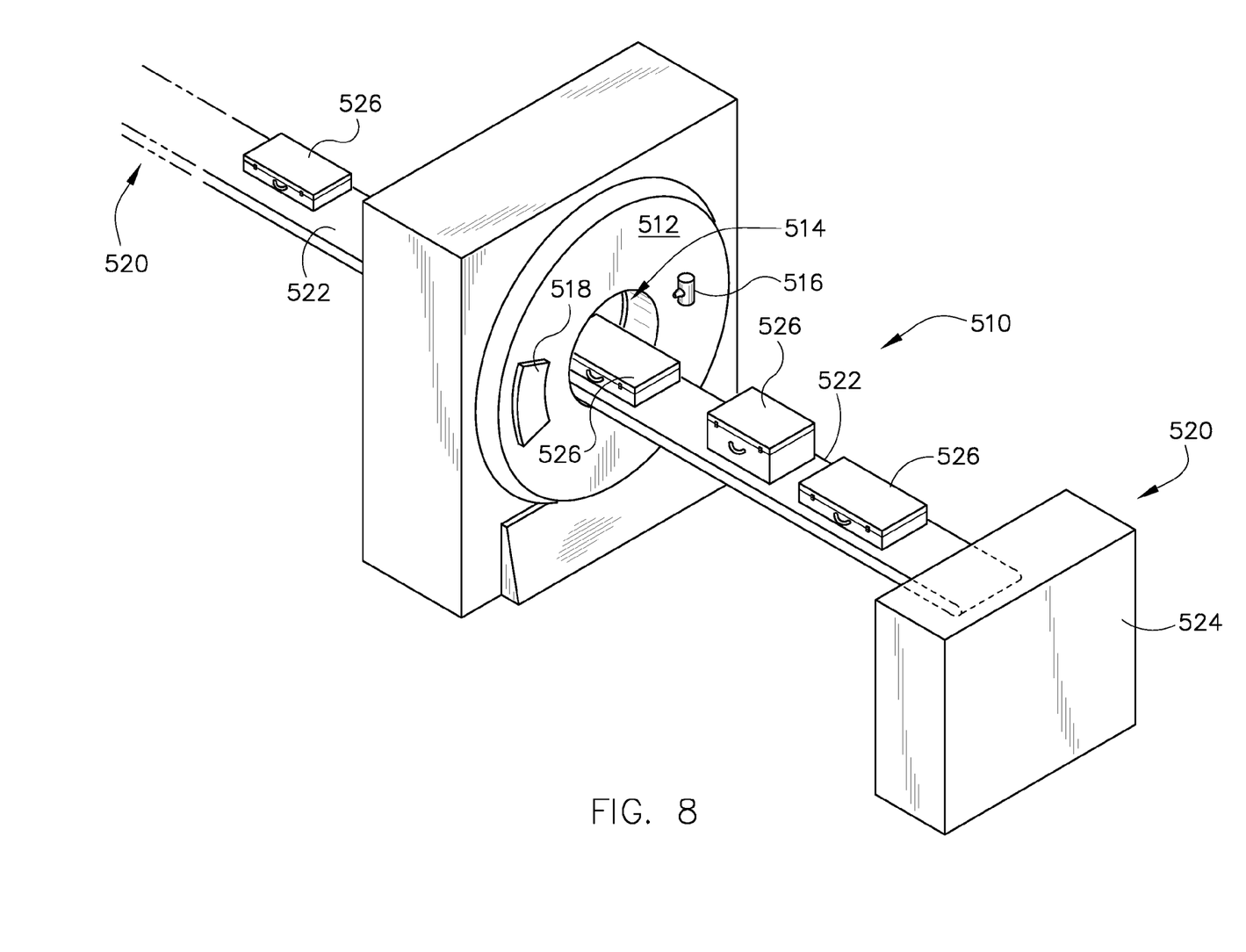
FIG. 8 is a pictorial view of a CT system for use with a non-invasive package inspection system.

Referring now to FIG. 8, package/baggage inspection system 510 includes a rotatable gantry 512 having an opening 514 therein through which packages or pieces of baggage may pass. The rotatable gantry 512 houses a high frequency electromagnetic energy source 516 as well as a detector assembly 518 having scintillator arrays comprised of scintillator cells similar to that shown in FIG. 4 or 5. A conveyor system 520 is also provided and includes a conveyor belt 522 supported by structure 524 to automatically and continuously pass packages or baggage pieces 526 through opening 514 to be scanned. Objects 526 are fed through opening 514 by conveyor belt 522, imaging data is then acquired, and the conveyor belt 522 removes the packages 526 from opening 514 in a controlled and continuous manner. As a result, postal inspectors, baggage handlers, and other security personnel may non-invasively inspect the contents of packages 526 for explosives, knives, guns, contraband, etc.

Therefore, according to an embodiment of the present invention, a CT imaging system includes a rotatable gantry having an opening to receive an object to be scanned, a first x-ray emission source attached to the rotatable gantry and configured to emit x-rays toward the object, and a second x-ray emission source attached to the rotatable gantry and configured to emit x-rays toward the object. A first detector is configured to receive x-rays that emit from the first x-ray emission source, and a second detector configured to receive x-rays that emit from the second x-ray emission source. A first portion of the first detector is configured to operate in an integration mode and a first portion of the second detector is configured to operate in at least a photon-counting mode.

According to another embodiment of the present invention, a method of x-ray imaging includes receiving x-rays in a first segment of a first detector array, the x-rays emitting from a first x-ray source that pass through at least a portion of an imaging region and receiving x-rays in a first segment of a second detector array, the x-rays emitting from a second x-ray source that pass through at least a portion of the imaging region. The method further includes operating the first segment of the first detector array in an integrating mode to generate a first set of data from received x-rays, operating the first segment of the second detector array in a photon-counting mode to generate a second set of data from received x-rays, and generating an image using the first and second sets of data.

According to yet another embodiment of the present invention, a CT imaging system includes a gantry configured to rotate about a subject and a pair of sources attached to the gantry configured to emit high frequency electromagnetic radiation toward the subject. A first array of detector modules is configured to receive high frequency electromagnetic radiation that emits from a first source of the pair of sources and passes through the subject, and a second detector module configured to receive high frequency electromagnetic radiation that emits from a second source of the pair of sources and passes through the subject. The first detector module is configured to operate in at least an integration mode and the second detector module is configured to operate in at least a photon-counting mode.

The present invention has been described in terms of the preferred embodiment, and it is recognized that equivalents, alternatives, and modifications, aside from those expressly stated, are possible and within the scope of the appending claims.

What is claimed is:

1. A CT imaging system comprising:
   a rotatable gantry having an opening to receive an object to be scanned;
   a first x-ray emission source attached to the rotatable gantry and configured to emit x-rays toward the object;
   a second x-ray emission source attached to the rotatable gantry and configured to emit x-rays toward the object;
   a first detector configured to receive x-rays that emit from the first x-ray emission source; and
   a second detector configured to receive x-rays that emit from the second x-ray emission source;
   wherein a first portion of the first detector is configured to operate in an integration mode, and a first portion of the second detector is configured to operate in at least a photon-counting mode.

2. The CT imaging system of claim 1 further comprising a computer programmed to correct saturated data in the second detector using non-saturated data from the first portion of the first detector.

3. The CT imaging system of claim 1 further comprising a dynamic bowtie filter positioned between at least one of the x-ray emission sources and its corresponding detector.

4. The CT imaging system of claim 1 wherein the first portion of the first detector comprises the entire first detector.

5. The CT imaging system of claim 4 wherein the first portion of the second detector comprises the entire second detector.

6. The CT imaging system of claim 4 wherein the second detector has a limited field-of-view (FOV), which is less than a FOV of the first detector.

7. The CT imaging system of claim 4 wherein the first x-ray emission source has a peak power capability greater than a peak power capability of the second x-ray emission source.

8. The CT imaging system of claim 1 wherein the second detector comprises a direct conversion detector configurable to operate either in the integration mode or the photon-counting mode.

9. The CT imaging system of claim 1 wherein a second portion of the second detector is configured to operate in at least the integration mode.

10. The CT imaging system of claim 9 wherein the first portion of the second detector is positioned to centrally receive a central beam of x-rays emitting from the second x-ray emission source.

11. The CT imaging system of claim 9 wherein the second portion of the second detector is configurable to operate in any of an integrating mode and a photon-counting mode.

12. The CT imaging system of claim 9 wherein the first detector has a limited field-of-view (FOV), which is less than a FOV of the second detector.

13. The CT imaging system of claim 9 wherein the second x-ray emission source has a peak power capability greater than a peak power capability of the first x-ray emission source.

14. A method of x-ray imaging comprising:
receiving x-rays in a first segment of a first detector array, the x-rays emitting from a first x-ray source that pass through at least a portion of an imaging region;
receiving x-rays in a first segment of a second detector array, the x-rays emitting from a second x-ray source that pass through at least a portion of the imaging region;
operating the first segment of the first detector array in an integrating mode to generate a first set of data from received x-rays;
operating the first segment of the second detector array in a photon-counting mode to generate a second set of data from received x-rays; and
generating an image using the first and second sets of data.

15. The method of claim 14 further comprising patching saturated data of the second segment using non-saturated data from the first segment.

16. The method of claim 15 wherein the step of patching further comprises patching the saturated data of the second segment using at least one iterative reconstruction technique.

17. The method of claim 15 wherein, during an axial scan, the patching of saturated data comprises:
shifting the saturated data by an integer number of views to account for an angular offset between the first and second detector arrays when the angular offset corresponds to an integer number of views; and
linearly interpolating the saturated data of the second segment from the non-saturated data of the first segment.

18. The method of claim 14 wherein receiving x-rays in the first segment comprises receiving x-rays in the entire first detector array, and wherein receiving x-rays in the second segment comprises receiving x-rays in the entire second detector array.

19. The method of claim 14 further comprising axially scanning or helically scanning the imaging region.

20. The method of claim 14 wherein the first segment of the first detector array comprises all detectors within the first detector array, and wherein the first segment of the second detector array consists of a subset of detectors that has less than all the detectors within the second detector array.

21. A CT imaging system comprising:
a gantry configured to rotate about a subject;
a pair of sources attached to the gantry and configured to emit high frequency electromagnetic radiation toward the subject;
a first array of detector modules configured to receive high frequency electromagnetic radiation that emits from a first source of the pair of sources and passes through the subject;
a second detector module configured to receive high frequency electromagnetic radiation that emits from a second source of the pair of sources and passes through the subject;
wherein the first detector module is configured to operate in at least an integration mode; and
wherein the second detector module is configured to operate in at least a photon-counting mode.

22. The CT imaging system of claim 21 wherein the first detector module comprises an array of detectors configured to operate in integration mode, and wherein the second detector module comprises an array of detectors configured to operate in photon-counting mode.

23. The CT imaging system of claim 22 wherein the array of detectors of the first detector module has a greater field-of-view (FOV) than the array of detectors of the second detector module, and wherein the first source has a peak power in excess of that of the second source.

24. The CT imaging system of claim 21 wherein the first detector module comprises an array of detector modules configurable to operate in either of an integrating mode and a photon-counting mode, and wherein the second detector module comprises:
a first array of detector modules configurable to operate in either of a photon-counting mode and an integration mode; and
a second array of detector modules configured to operate in integration mode.

25. The CT imaging system of claim 21 further comprising a data processor configured to correct saturated data in the second detector module from non-saturated data in the first detector module.

* * * * *